United States Patent
Errico et al.

(10) Patent No.: US 6,780,186 B2
(45) Date of Patent: Aug. 24, 2004

(54) ANTERIOR CERVICAL PLATE HAVING POLYAXIAL LOCKING SCREWS AND SLIDING COUPLING ELEMENTS

(75) Inventors: Joseph P. Errico, Kirkland, WA (US); Thomas J. Errico, Summit, NJ (US); James D. Ralph, Seaside Park, NJ (US)

(73) Assignee: Third Millennium Engineering LLC, Summit, NJ (US)

( * ) Notice: Subject to any disclaimer, the term of this patent is extended or adjusted under 35 U.S.C. 154(b) by 416 days.

(21) Appl. No.: 10/016,776

(22) Filed: Nov. 2, 2001

(65) Prior Publication Data

US 2002/0045899 A1 Apr. 18, 2002

Related U.S. Application Data

(63) Continuation-in-part of application No. 09/774,915, filed on Jan. 30, 2001, now Pat. No. Re. 37,665, and a continuation-in-part of application No. 08/788,804, filed on Jan. 23, 1997, now Pat. No. 5,817,094, and a continuation-in-part of application No. 08/632,560, filed on Apr. 15, 1996, now Pat. No. 5,725,588, which is a continuation-in-part of application No. 08/624,110, filed on Mar. 29, 1996, now Pat. No. 5,876,402, which is a continuation-in-part of application No. 08/421,087, filed on Apr. 13, 1995, now Pat. No. 5,520,690.

(51) Int. Cl.$^7$ .................................. A61B 17/80
(52) U.S. Cl. ........................................... 606/71; 606/61
(58) Field of Search .............................. 606/61, 69, 70, 606/71

(56) References Cited

U.S. PATENT DOCUMENTS

| 5,735,853 | A | * | 4/1998 | Olerud .......................... 606/71 |
| 5,954,722 | A | * | 9/1999 | Bono ............................ 606/61 |
| 6,030,389 | A | * | 2/2000 | Wagner et al. ................. 606/71 |

* cited by examiner

Primary Examiner—David O. Reip

(57) ABSTRACT

A polyaxial locking cervical screw and plate assembly for immobilization of cervical bones, via fixation to surfaces thereof, including a plate, having a pair of elongated tapered holes in the top and bottom thereof, into which holes elongated coupling elements and screws may be inserted. Each coupling element has an equivalent taper which matches the taper of the holes in the plate, and an interior semi-spherical curvate surface in which the curvate head of the screw may be polyaxially mounted. The coupling elements are initially disposed in the holes in the plate such that they may slide axially therein. The bone screws are inserted through the respective coupling elements until the heads thereof enter the curvate volumes thereof. Once the head is fully seated in the coupling element, advancement of the screw causes the coupling element to crush lock to the plate and to the head of the screw.

7 Claims, 3 Drawing Sheets

ANTERIOR CERVICAL PLATE HAVING POLYAXIAL LOCKING SCREWS AND SLIDING COUPLING ELEMENTS

CROSS-REFERENCE TO RELATED APPLICATIONS

The present application is a continuation-in-part of applications U.S. Ser. No. 08/624,110 filed Mar. 29, 1996, Ser. No. 08/632,560 filed Apr. 15, 1996, and Ser. No. 08/788,804, filed Jan. 23, 1997, entitled, "Anterior Spinal Polyaxial Locking ScrewPlate Assembly Having Recessed Retaining Rings", "Acetabular Cup Having Polyaxial Locking Screws", and "A Polyaxial Locking Screw And Rod Coupling Element", respectively, which are now issued as U.S. Pat. Nos. 5,876,402; 5,725,588; and 5,817,094, respectively. Each of said applications was in turn a continuation-in-part of U.S. Ser. No. 08/421,087 filed Apr. 13, 1995 now issued U.S. Pat. No. 5,520,690, entitled "A Posterior Spinal Polyaxial Locking Screw Plate Assembly". The present application is also a continuation-in-part of co-pending reissue application U.S. Ser. No. 09/774,915, filed Jan. 30, 2001 now U.S. Pat. No. RE37,655 entitled "Polyaxial Pedicle Screw Having a Threaded and Tapered Compression Locking Mechanism".

FIELD OF THE INVENTION

This invention relates generally to a cervical spinal implant assembly for holding adjacent vertebral bones fixed, and more particularly to a cervical plate assembly having polyaxial screws which seat into sliding and locking socket components.

BACKGROUND OF THE INVENTION

The bones and connective tissue of an adult human spinal column consists of more than 20 discrete bones coupled sequentially to one another by a tri-joint complex which consist of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

Genetic or developmental irregularities, trauma, chronic stress, tumors, and disease are a few of the causes which can result in spinal pathologies for which permanent immobilization of multiple vertebrae may be necessary. A variety of systems have been disclosed in the art which achieve this immobilization by implanting artificial assemblies in or on the spinal column. These assemblies may be classified as anterior, posterior, or lateral implants. As the classification suggests, posterior implants are attached to the back of the spinal column, generally hooking under the lamina and entering into the central canal, attaching to the transverse process, or coupling through the pedicle bone. Lateral and anterior assemblies are coupled to the vertebral bodies.

The region of the back which needs to be immobilized, as well as the individual variations in anatomy, determine the appropriate surgical protocol and implantation assembly. Posterior fixation is much more commonly used in the lower back, i.e., the sacral, lumbar, and lower thoracic regions, than in the upper regions of the thoracic and the cervical spine. The use of screw and plate assemblies for stabilization and immobilization via lateral or anterior entrance in these upper regions is, however, common.

Because the cervical spine is routinely subject to mechanical loads which cycle during movement, one of the primary concerns of physicians performing cervical plate implantation surgeries, as well as of the patients in whom the implants are placed, is the risk of screw pullout. This is of particular concern in the cervical region because of the critical vessels which abut the anterior surfaces of the cervical spine. Screw pull-out occurs when the cylindrical portion of the bone which surrounds the inserted screw fails. A bone screw which is implanted perpendicular to the plate is particularly weak because the region of the bone which must fail for pull-out to occur is only as large as the outer diameter of the screw threads. It has been found that for pull-out to occur for a pair of screws which are angled inward, "toe nailed", or ones which diverge within the bone, the amount of bone which must fail increases substantially as compared to pairs of screws which are implanted in parallel along the axis that the loading force is applied. It has, therefore, been an object of those in the art to provide a screw plate assembly which permits the screws to be entered into the vertebral body at angles other than 90 degrees.

As mentioned above, a great concern with screws being implanted in the anterior portion spine, most particularly in the cervical spine, is that their are important internal tissue structures which, because of their proximity to the implant, may be damaged by a dislocated screw. In the cervical spine, the esophagus is located directly in front of the anterior surface of the vertebral body, and therefore, in potential contact with an implanted cervical plate. Breaches of the esophageal wall permit bacterial contamination of the surrounding tissues, including the critical nerves in and around the spinal cord. Such contamination can be fatal. Because screw pull-out represents one of the largest risks of esophageal perforation, it has been an object of those in the art to produce a cervical screw plate design having a locking means which couples, not only the plate to the bone, but locks the screw to the plate. In such a design, it is intended that, even if the bone holding the screw fails, the screw will not separate from the plate.

One screw plate design which has been offered to provide physicians and patients with a reduced risk of pull-out or damage to proximal tissues is the Orion (Reg. Trademark) Anterior Cervical Plate System of Sofamor Danek USA, 1800 Pyramid Place, Memphis, Tenn. 38132. The Orion™ system teaches a plate having two pair of guide holes through which the screws are inserted to fix the plate to the vertebral body. The plate further includes external annular recessions about each of the guide holes which are radially non-symmetric in depth. More particularly, the annular recessions serve as specific angle guides for the screws so that they may be inserted non-perpendicularly with respect to the overall curvature of the plate. In addition, the Orion™ plate includes an additional threaded hole disposed between each of the pairs of guide holes so that a corresponding set screw may be inserted to lock the bone screws to the plate.

Although the Orion™ system achieved certain advantages over prior cervical screw plate assemblies, it is not without substantial drawbacks. Specifically, a given plate can accommodate only one screw-in angulation per hole, preferably in accordance with the angle of the annular recession. This is undesirable, in that physicians often must inspect the vertebral bodies during the implantation procedure before making the decision as to which screw-in angle is the ideal. By forcing the physician to chose from a limited set of angles, it is unavoidable that physicians will be forced to implant plates having screws which were positioned non-ideally. While providing a variety of plates having different angle guide holes and annular recession orientations is possible, the complexity and expense of providing a full spectrum of plates available in the operating room for the surgeon to choose from is undesirable. It is a failure of the system that one plate cannot accommodate a variety of different screw-in angles.

It is further a failure of the Orion™ system that an extra set screw is required to lock the screw to the plate. Plates for use in the cervical spine are very thin, and if the screw head already rests in an annular recess, and there is to be enough room for the head of the set screw to rest on top of the head of the bone screw, the thickness of the remaining plate must be reduced even further. The thinner the plate is at the load bearing points—the guide holes—the weaker the plate is overall.

Another critical failure of the Orion™ plate, is its inability to permit variation in the screw insertion point relative to the plate and other screws. More particularly, it is often desirable for the surgeon to be able to insert a screw at a slightly different point on the cervical one on one lateral side as compared with the opposite lateral side. With the Orion™ plate, a surgeon would have to offset the entire plate in order to accommodate this relative screw positioning offset. It would therefore be a significant advantage to provide a plate which permits relative screw offset without having to offset the plate itself.

While the preceding discussion has focused on a specific cervical screw plate system and its failures, the same failures apply to the art of lumbar and thoracic immobilizing screw plate systems which are presently available as well. It is therefore, an object of the present invention to provide a new and novel cervical, thoracic, and/or lumbar screw plate design having a polyaxial coupling of the screw to the plate, whereby a single plate is compatible with a wide range of screw-in angles.

It is also an object of the present invention to provide an orthopedic screw plate assembly which has a simple and effective locking mechanism for locking the bone screw to the plate.

It is still further an object of the present invention to provide a screw plate assembly having a retaining means for preventing screw pull-out in the event of a failure of the locking mechanism.

It is also an important object of this invention to provide a screw and plate assembly which can accommodate a variety of different screw insertion points without requiring an offset of the plate itself.

Other objects of the present invention not explicitly stated will be set forth and will be more clearly understood in conjunction with the descriptions of the preferred embodiments disclosed hereafter. into the tapered through hole. As the tapered surface of the coupling element advances, the lateral constraining forces of the mutual tapers (of the coupling element and the through hole) causes the element to contract slightly as the axial slot or slots are narrowed. This contraction causes the interior volume to crush-lock to the semi-spherical head of the screw thereby locking it at the given angulation and to the plate.

DETAILED DESCRIPTION OF THE PREFERRED EMBODIMENT

While the present invention will be described more fully hereinafter with reference to the accompanying drawings, in which particular embodiments and methods of fabrication are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1B:
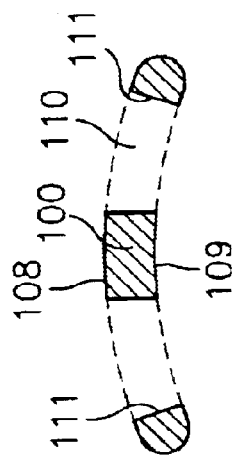
FIGS. 1a and 1b are top and cross-sectional views, respectively, of a locking plate having elongate tapered through holes which is a feature of the present invention.
Figure 1A:
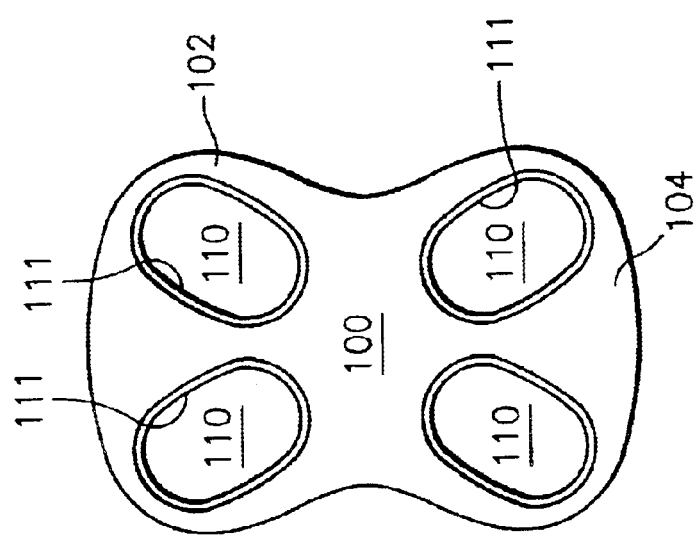

Referring now to FIGS. 1a and 1b, a plate which is an element of the present invention is shown in perspective and top views, respectively. The plate 100 may be constructed of any suitably biocompatible material which has the structural strength and durability to withstand the cyclical loading associated with long term fixation to the cervical spine. Materials which would be suitable for such applications include titanium alloys and steels. A specific titanium material which has been utilized in implants of the prior art include ASTM F-136 titanium alloy (Ti 6AL-4V). This material has enhanced mechanical properties including fatigue endurance and tensile strength, as compared with pure titanium.

The plate 100 comprises upper and lower portions 102, 104 respectively, and a top surface 108 and a bottom surface 109. A slight curvature may be imparted to the plate 100 so that it may grossly conform to the cylindrical morphology of the vertebral bodies to which it is to be coupled. The curvature would correspondingly be such that the top surface 108 would be convex surface, and the bottom surface 109 would be concave.

A pair of elongate tapered through holes 110, having smoothly tapered inner elongate surfaces 111, extend fully through each of the upper and lower portions 102,104 of the plate. Each of the holes 110 is ideally suited for slidably retaining an elongate coupling element (see the description provided hereinbelow with reference to FIG. 2) therein.

Figure 2:
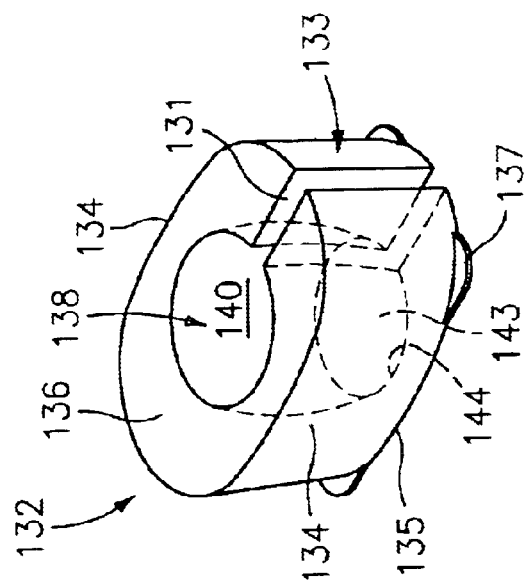
FIG. 2 is a side perspective view of the elongated coupling element which seats in the elongate tapered through holes of the plate illustrated in FIGS. 1a and 1b.

Referring now to FIG. 2 the elongate coupling element 132, which is utilized in conjunction with the plate 100 shown in FIGS. 1a and 1b, is shown in a side perspective view, wherein phantom lines show the interior structure of the element along a diametrical cross-section. The coupling element 132 comprises a socket having lateral tapered sides 134 which are designed to nest within the tapered walls 111 and slide axially along the elongate through holes 110 of the plate 100.

The top surface 136 of the elongate coupling element 132 further comprises a through hole 138, which extends from the top surface 136 to an interior semi-spherical volume 140. This through hole 138 is designed such that a screw (see FIG. 3, and the corresponding description provided below) may be inserted and advanced therethrough.

The coupling element 132 also comprises at least one slot 131 formed in the non-tapered front (and/or rear) surface 133—rear surface not shown—which extends upward through at least part of the way from the bottom of the coupling element to the top. In a preferred embodiment, the element 132 comprises a single axial slot 131 which extends fully up the element 132 so that it has a circumferentially discontinuous conformation. This slot 131 permits the coupling element 132 to expand and /or contract in accordance with the application of a corresponding radial opening or closing force.

The bottom exterior surface 135 of the elongate coupling element 132 further includes an outwardly extending lip 137. This lip 137 would otherwise prevent insertion of the coupling element 132 fully into the elongate tapered through hole 110, however, the closing action of the slot 131 permits the lip to slide past the narrower bottom portion of the tapered through hole 110 and snap into position. Once in position, the coupling element 132 is slidably moveable within the elongate through hole 110, but is not easily removable therefrom by virtue of the interference of the lip 137 and the bottom edge of the through hole 110.

Figure 3:
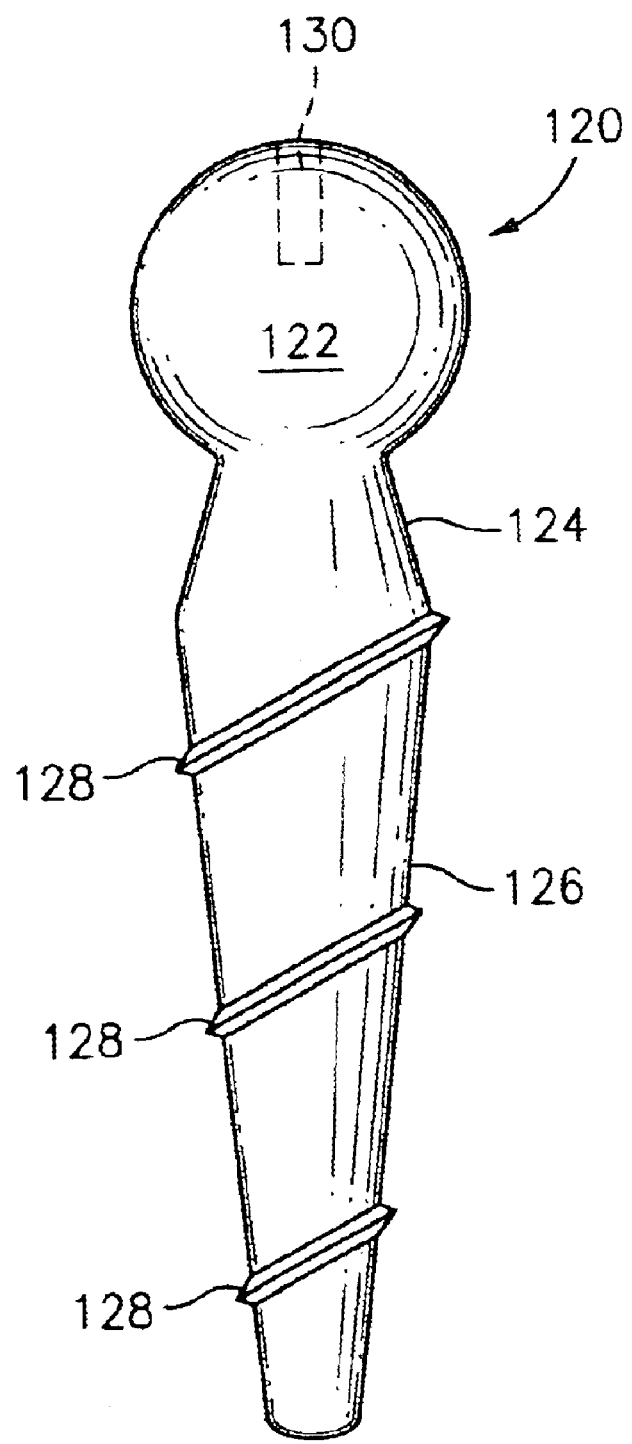
FIG. 3 is a perspective view of a bone screw of the present invention.

Referring now to FIG. 3, a screw of a type which is ideally suited for coupling the plates of this invention to vertebral bodies (or long bones in other embodiments) is shown in a side view. The screw 120 comprises a head portion 122, a neck 124, and a shaft 126. In FIG. 3, the shaft 126 is shown as having a tapered shape with a high pitch thread 128. It shall be understood that a variety of shaft designs are interchangeable with the present design. The specific choice of shaft features, such as thread pitch, or shaft diameter to thread diameter ratio, or overall shaft shape, etc. should be made be the physician with respect to the conditions of the patient's bone, however, this invention is compatible with a wide variety of shaft designs.

The head portion 122 of the screw 120 comprises a semi-spherical shape, which has a recess 130 in it. It is understood that the semi-spherical shape is necessarily is a section of a sphere, greater in extent than a hemisphere, and exhibits an external contour which is equidistant from a center point of the head. In a preferred embodiment, the major cross-section of the semi-spherical head 122 (as shown in the two dimensional illustration of FIG. 3) includes at least 270 degrees of a circle.

The recess 130 defines a receiving locus for the application of a torque for driving the screw 120 into the bone. The specific shape of the recess 122 may be chosen to cooperate with any suitable screwdriving tool. For example, the recess 130 may comprise a slot for a flatheaded screwdriver, a crossed recess for a phillips head screwdriver, a hexagonally shaped hole for receiving an allen wrench, or most preferably, a threading for receiving a correspondingly threaded post. It is further preferable that the recess 130 be co-axial with the general elongate axis of the screw 120, and most particularly with respect to the shaft 126. Having the axes of the recess 130 and the shaft 126 co-linear facilitates the step of inserting the screw 120 into the bone.

The semi-spherical head portion 122 is connected to the shaft 126 at a neck portion 124. While it is preferable that the diameter of the shaft 126 be less than the radius of the semi-spherical head 122, it is also preferable that the neck 124 of the screw 120 be narrower than the widest portion of the shaft 126. This preferable dimension permits the screw to be inserted at a variety of angles while still permitting the specific coupling element to be screwed into the appropriate hole 110 or 112 of the plate 100 and remain coupled to the head 122.

Referring again to FIG. 2, the coupling element 132 further includes an interior semi-spherical volume 140 which is ideally suited for retaining holding the head portion 122 of the screw 120, and permitting the introduction of the screw therethrough at wide a range of angles including non-perpendicular angles. The bottom 135 of the coupling element 132 has a circular hole (enumerated as 143 on the bottom surface of the side view of the coupling element) which forms the bottom entrance into the interior semi-spherical volume 140. It is understood that the head 122 of the screw 120 is held within the interior semi-spherical volume 140 by the inner annular rim, 144 of the bottom 142 of the coupling element. This inner annular rim 144 defines the circular opening 143 which has a diameter less than the diameter of the semi-spherical head 122 of the screw 120, but larger than the neck 124 of the screw 120.

Figure 4B:
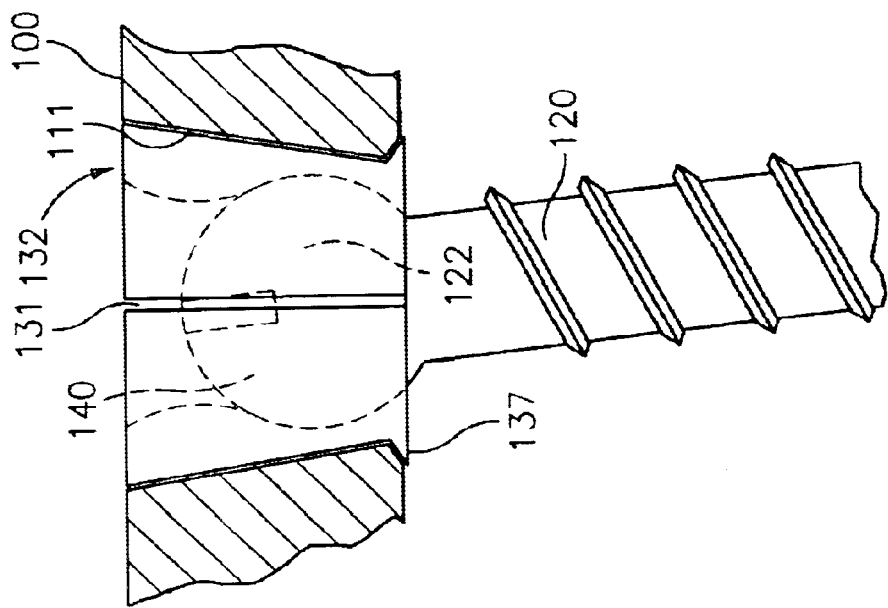
FIGS. 4a and 4b are side cross-section views of a partially and a fully assembled embodiment of the present invention, respectively.
Figure 4A:
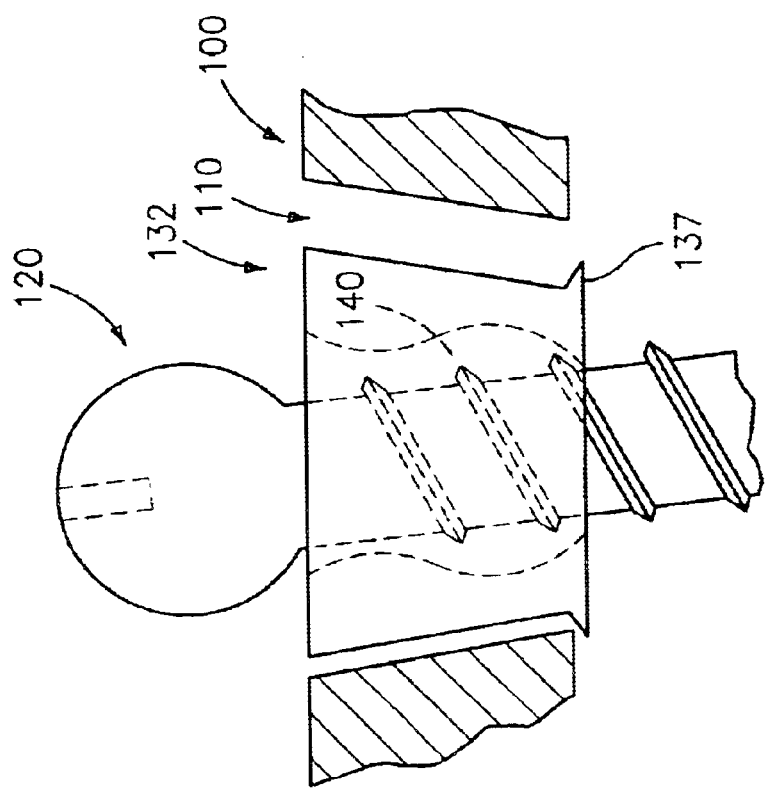

Referring now to FIGS. 4a and 4b, the pre-assembled and fully assembled screw 120, elongate coupling element 132, and plate 100 are shown, respectively, in cross-section views. As stated previously, the coupling element 132 is snapped into the corresponding elongated tapered through hole 110 of the plate 100. In this initial position, the coupling elements 132 are free to be independently and selectively moved by the surgeon, within the through holes, into the ideal position relative to the vertebral bone to which the assembly is to be affixed. The lower outer lip 137 of the coupling element 132 prevents the coupling element from falling out of the plate 110 in this initial position. Once properly positioned, the surgeon drills holes into the bone in order to prepare the sites for the screws 120 to be advanced thereinto. The screws 120 are then advanced through the interior 140 of the coupling element 132 until the head 122 thereof seats into the interior volume 140 and is prevented from continued independent advancement by virtue of its interaction with the coupling element 132. Continued advancement, therefore, of the screw is combined with the movement of the coupling element 132 deeper into the tapered through hole 110. This movement of the coupling element relative to the tapered walls 111 of the holes causes the slot 131 of the coupling element to close. This closing causes the head 122 of the screw to become locked within the coupling element 132. In addition, this closing force provides a tapered friction lock of the coupling element 132 deep within the through hole 110, thus locking the entire assembly together.

While there has been described and illustrated a cervical implantation device for stabilizing and immobilizing regions of the cervical spine by affixing a polyaxial locking screw plate to the anterior portion of adjacent bones, it will be apparent to those skilled in the art that variations and modifications are possible without deviating from the broad spirit and principle of the present invention which shall be limited solely by the scope of the claims appended hereto.

We claim:

1. A polyaxial locking screw plate assembly comprising:
   a plate having a plurality of through holes, at least one said through holes being elongated in the plane of the plate and including opposing tapered side walls;
   a corresponding at least one coupling element, said at least one coupling element including a central hole for receiving a screw therethrough and opposing tapered exterior surfaces such that said at least one coupling element may initially slide along an elongate axis of said corresponding elongate through hole when said coupling element is loosely nested therein; and at least one corresponding screw having a head portion and a shaft portion, said shaft portion being insertable through the corresponding central hole in said corresponding at least one coupling element, and said head portion being larger than necessary to travel through the central hole in the coupling element such that advancement of said shaft portion through said central hole causes the head portion to engage the coupling element and to cause the coupling element to be driven into the corresponding through hole of the plate such that the coupling element and the plate are crush locked together be virtue of their mutual tapers.

2. The assembly as set forth in claim 1, wherein said at least one coupling element further comprises an axial slot formed therein which slot permits the expansion and contraction of the central hole by means of a lateral force applied to the opposing tapered exterior surfaces thereof.

3. The assembly as set forth in claim 2, wherein said coupling element further comprises a lower outer lip which engages a lower edge of said elongate tapered through hole of said plate such that said coupling element is initially slideably retained within said through hole.

4. The assembly as set forth in claim 2, wherein said central hole further comprises a curvate interior volume, and wherein said screw includes a curvate head portion which seats in said curvate interior volume, and wherein said curvate head portion is crush locked therein by the application of a lateral force against the opposing tapered exterior surfaces of the coupling element by the opposing tapered side walls of the elongate through hole into which it is driven and which causes the contraction of the central hole.

5. The assembly as set forth in claim 1, wherein said central hole further comprises a curvate interior volume, and wherein said screw includes a curvate head portion which seats in said curvate interior volume.

6. The assembly as set forth in claim 1, wherein the head portion of said at least one screw comprises a recess to which a screwdriving tool is mateable for inserting said screw through the corresponding central hole.

7. A polyaxial locking screw plate assembly comprising:

a plate having a plurality of through holes, at least one said through holes being elongated in the plane of the plate and including opposing tapered side walls;

a corresponding at least one coupling element, said at least one coupling element including a central hole for receiving a screw therethrough, said hole including a curvate interior volume, and said coupling element further including opposing tapered exterior surfaces such that said at least one coupling element may initially slide along said elongate axis of said corresponding elongate through hole when loosely nested therein, and further including at least one axial slot such that said coupling element and said interior volume may expand and contract by the application of lateral forces acting upon said opposing tapered exterior surfaces; and at least one corresponding screw having a curvate head portion and a shaft portion, said shaft portion being insertable through the corresponding central hole in said corresponding at least one coupling element within a range of angles including non-perpendicular angles, and a curvate head portion having a diameter which is greater larger than necessary to travel fully through the central hole in the coupling element, but which seats fully in said curvate interior volume thereof, such that advancement of said shaft portion through said central hole causes the head portion to enter the interior volume and to cause the coupling element to be driven into the corresponding through hole of the plate such that the coupling element and the plate are crush locked together be virtue of their mutual tapers, and such that the curvate head is locked within the curvate interior volume of the coupling element by virtue of the contraction of the axial slot.

\* \* \* \* \*